(12) United States Patent
Sperling

(10) Patent No.: US 7,184,147 B2
(45) Date of Patent: Feb. 27, 2007

(54) DEVICE FOR DETERMINING THE PROPERTIES OF SURFACES

(75) Inventor: Uwe Sperling, Geretsried (DE)

(73) Assignee: BYK Gardner GmbH, Geretsried (DE)

(*) Notice: Subject to any disclaimer, the term of this patent is extended or adjusted under 35 U.S.C. 154(b) by 347 days.

(21) Appl. No.: 10/880,361

(22) Filed: Jun. 29, 2004

(65) Prior Publication Data
US 2005/0073688 A1 Apr. 7, 2005

(30) Foreign Application Priority Data
Jul. 3, 2003 (DE) .................. 103 30 071

(51) Int. Cl.
G01N 21/55 (2006.01)
G01N 21/00 (2006.01)

(52) U.S. Cl. ............................ 356/445; 356/237.2

(58) Field of Classification Search ............. None
See application file for complete search history.

(56) References Cited

U.S. PATENT DOCUMENTS

| | | | |
|---|---|---|---|
| 5,923,419 A * | 7/1999 | Thomas | 356/239.4 |
| 7,042,581 B2 * | 5/2006 | Schietinger et al. | 356/630 |
| 2004/0239919 A1 * | 12/2004 | Schwarz | 356/237.2 |

* cited by examiner

Primary Examiner—Michael P. Stafira
(74) Attorney, Agent, or Firm—Greer, Burns & Crain, Ltd.

(57) ABSTRACT

A device for determining the properties of surfaces having at least one first radiation means having a least one radiation source which emits radiation, at least one radiation detector means which captures at least a portion of the radiation emmitting from the at least one radiation source and then diffused and/or reflected off a measurement surface and emits at least one measurement signal which is characteristic of the reflected and/or diffused radiation, an optical divider means having a specified thickness positioned in the optical path between the radiation means and the radiation detector means. The optical divider means includes at least one aperture extending at least in sections at a specified angle different from 0 degrees to the thickness of said optical divider means.

26 Claims, 2 Drawing Sheets

DEVICE FOR DETERMINING THE PROPERTIES OF SURFACES

BACKGROUND

The present invention relates to a device for determining the properties of surfaces such as in particular but not exclusively their color.

The optical impression of objects or their surfaces, in particular the surfaces of motor vehicles, is decisively determined by the surface qualities. Since the capability of the human eye to objectively evaluate properties of surfaces is limited, there is a need of auxiliaries and devices for qualitatively and quantitatively determining the properties of surfaces.

The properties of surfaces determined are for example gloss, orange peel, color, macro- and/or micro texture, distinctness of image, haze, surface texture and/or topography, and the like.

Devices are known from the prior art in which a radiation means projects radiation onto the measuring surface to be examined and the radiation reflected and/or diffused off said measuring surface is captured and evaluated by a detector. The problem is to project the radiation onto the measuring surface in comparable conditions so as to allow an evaluation of the surface to be examined. There is for example but not exclusively the problem that radiation must be projected to the measuring surface to be examined at a specified angle.

SUMMARY

The device of the present invention for determining the properties of surfaces comprises at least one first radiation means having at least one radiation source which emits radiation. In addition, a radiation detector means is provided which captures at least a portion of the radiation emitting from the at least one radiation source and then diffused and/or reflected off a measurement surface, which emits at least one measurement signal characteristic of at least one parameter of the reflected and/or diffused radiation.

Furthermore, an optical divider means having a specified thickness is provided which is positioned in the optical path between the radiation means and the radiation detector means. Said optical divider means comprises at least one aperture extending at least in sections at a specified angle different from 0° to the thickness of said optical divider means.

A measuring surface is understood to mean every surface reflecting and/or diffusing at least a portion of captured incident radiation. Measuring surfaces within the scope of the present invention are in particular understood to mean surfaces of motor vehicles such as in particular but not exclusively their finished surfaces.

A characteristic measurement signal is understood to mean a measurement signal depending on at least one parameter of the incident radiation such as its intensity, wavelength or the like. A measuring surface may in addition mean the marbled effect of plastics or of individually manufactured or processed materials.

An optical divider means is understood to mean a device capable of blocking optical radiation, in particular light—in particular but not exclusively—in the visible range, or of inhibiting passage of at least a portion of said light in a specified optical path.

An aperture extending at least in sections at a specified angle different from 0° to the thickness is understood to mean an aperture extending not perpendicular to the surface of the divider means but at a specified angle thereto.

The term aperture within the scope of the present invention is understood to mean segments of surfaces or spaces within which there are spaces at least a portion of which is devoid of substance. An aperture is thus understood to include slits, slots, and the like.

In another preferred embodiment a top view of the aperture of the optical divider means shows it to be substantially circular or a circular slot in shape. This is to be understood such that for example in a specified cross-sectional area of the optical divider means the aperture in the cross section of a circle is a circle line of a specified thickness. Herein the shape of a circular periphery is substantially understood to include such shapes where said circle is interrupted, in particular but not exclusively by individual ridges of different widths.

A view of the entire divider means including its thickness shows the cross-section of the aperture to be a circular periphery and a three-dimensional view shows the shape of a cone or a cone section at a specified cone angle. In other words, at least one wall of the aperture or the slit is substantially defined by the circumferential surface of a cone.

In another preferred embodiment the interior surfaces of the aperture have substantially radiation-absorbing properties, in particular relative the radiation passing through it. In this way it can be achieved that radiation passing through said aperture does not reflect off the interior faces of the aperture.

In another preferred embodiment the angle at which the aperture extends to the thickness of the optical divider means is between 0 and 90°, preferred between 15° and 75°, particularly preferred between 30° and 60° and in particular in the range of 45°. It is preferred that the optical divider means is positioned parallel to the measuring surface. This means that radiation passing through this aperture impinges on the measuring surface substantially at the specified angle.

In another preferred embodiment the optical divider means has at least partially reflecting and/or diffusing properties relative radiation emitting from the radiation means at least at one surface facing the at least one radiation detector means. It is preferred that as large a portion as possible of the radiation emitting from the radiation means diffuses and/or reflects off the respective surface of the optical divider means.

In another preferred embodiment the optical divider means is single-piece. At the surface facing the radiation means said optical divider means has a coating that preferably reflects and/or diffuses said radiation as specified above. In this case it is preferred to provide an aperture extending, as described above, substantially along a circle line but interrupted by a number of ridges. In another preferred embodiment the optical divider means consists at least of two components. These two components are joined preferably by form-fitting, force-closed and/or firm connections selected from a group of connections including bonding, soldering and the like. In such a case that component facing the optical radiation means or its surface facing the optical radiation means must exhibit at least some radiation-reflecting and/or diffusing properties.

In a preferred embodiment a plurality of first radiation means is provided which are arranged at predetermined positions relative the measuring surface. These positions may be arranged such that they are substantially equidistant from the measuring surface.

It is preferred that the first radiation means are arranged in a first housing section. Said first housing section is substantially hemispherical in shape. It is preferred that a plurality of radiation means are arranged substantially at an azimuth circle of the substantially hemispherical housing.

In another preferred embodiment a reference measurement means is arranged in the first housing. Said reference measurement means serves to capture at least a portion of the radiation emitting from the plurality of radiation means preferably after at least one single diffusion and/or reflection so as to use it as a reference value for the portion of radiation captured by the radiation detector means. For this purpose the reference measurement means comprises an optical barrier which causes that the light from the radiation means cannot directly enter into the reference measurement means but is first reflected and/or diffused off at least one surface, in particular but not exclusively a surface of the optical device.

In another preferred embodiment the first housing section exhibits at least at one portion of its surface facing the measuring surface radiation-reflecting and/or radiation-diffusing properties. In the case of a substantially hemispherical housing, the surface facing the measuring surface is the inner surfaces of said housing. In this way the aim is achieved that the light emitting from the radiation means is repeatedly reflected at the inside of the first housing section before it impinges on the measuring surface through the aperture.

In another preferred embodiment at least one radiation means comprises a radiation diffusor means. Said radiation diffusor means ensures that the light emitting from the radiation source or the radiation means diffuses such that substantially diffused light is generated.

The at least one radiation diffusor means is selected from a group of radiation diffusor means including radiation diffusor disks, frosted glass disks, diffusor films and the like.

In another preferred embodiment at least one first radiation means comprises at least one radiation source selected from a group of radiation sources comprising thermal radiation sources, in particular but not exclusively light bulbs, halogen light bulbs, coherent and non-coherent semiconductor radiation sources, gas discharge radiation sources, lasers and the like. The emitted radiation is preferably, but not exclusively, light in the visible spectrum. However, light in the infrared and/or ultraviolet spectral ranges may also be used. A use of X-ray or similar beams also lies within the scope of the present invention.

It is preferred that at least two radiation sources exhibit different radiation characteristics. In a preferred embodiment a plurality of radiation sources having different spectral radiation characteristics are selected so as to cover substantially the entire visible spectral range. In another preferred embodiment the quantity of the individual radiation sources is selected such that the light or its intensity is substantially uniform over the entire visible spectral range. Substantially uniform is understood to mean that the intensity remains around a predetermined mean value in the entire visible spectral range at deviations between 50% and 200% from the mean value, preferred between 40% and 150% and particularly preferred between 80% and 120%.

In another preferred embodiment at least one radiation means is variable relative at least one radiation parameter selected from a group of parameters comprising radiation intensity, radiation wavelength, direction of radiation polarization, temporal radiation intensity modulation and the like. Radiation intensity modulation is understood to mean that within a specified period the intensity can be varied or the associated radiation source can be switched on or off.

In another preferred embodiment at least the first radiation detector means is arranged in a second housing section.

The second housing section exhibits radiation-absorbing properties at least at one portion of the surfaces facing the radiation detector means. This is understood to mean that light impinging on these surfaces through the optical divider means is substantially absorbed. Preferably at least all of the surfaces facing the radiation detector means, preferably all the inner surfaces, of the second housing section exhibit radiation-absorbing properties. In this way the aim is achieved that no light reflected and diffused in the second housing section can enter into the first radiation detector means but substantially only light reflected and/or diffused off the measuring surface.

In another preferred embodiment substantially no external radiation enters the second housing unless it has been diffused and/or reflected off the measuring surface. This means that, apart from one aperture facing the measuring surface, the housing has no other apertures through which light from outside could enter into the second housing section.

The invention further relates to a method for determining the properties of surfaces. In a first process step, a first radiation emits from at least one first radiation means according to the claims specified above. Said radiation is diffused and/or reflected off at least one surface and directed through an aperture according to at least one of the preceding claims. In a following process step said radiation is directed toward a measuring surface and finally the radiation diffused and/or reflected off the measuring surface is at least partially captured by a radiation detector means according to at least one of the preceding claims.

Preferably the radiation emitting from the first radiation means is repeatedly reflected and/or diffused off the inner surface of the first housing section. In this way the properties of the light impinging onto the measuring surface are enhanced.

DETAILED DESCRIPTION OF THE PREFERRED EMBODIMENT

Figure 1:
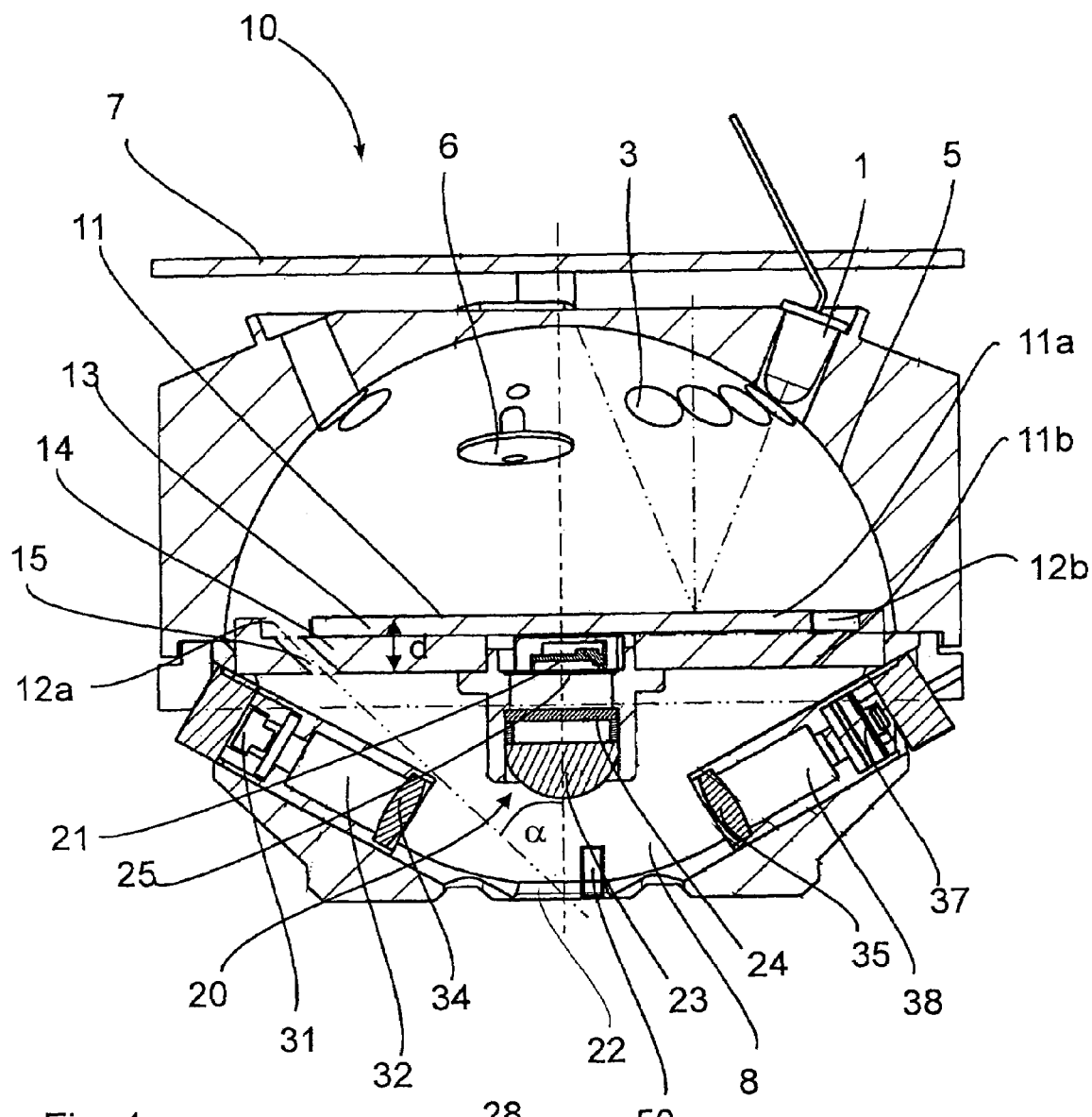
FIG. 1 depicts the device of the invention for determining the properties of surfaces.

FIG. 1 shows the device of the invention for determining the properties of surfaces. Reference numeral 1 indicates a first radiation means. In the present case this is a light-emitting diode. Said light-emitting diode is positioned in an aperture 3 of the first housing section 5. Preferably a plurality of first radiation means 1 is arranged in a plurality of apertures 3. The individual radiation means or their light-emitting diodes exhibit preferably different radiation characteristics, in particular they emit light of different wavelengths.

Reference numeral 6 indicates a reference measurement means. Said reference measurement means comprises a radiation blocking means to prohibit light from directly entering into the reference measurement means 6 from the radiation means 1. It is rather intended that substantially only such light enters into the reference measurement means which has been diffused and/or reflected at least twice, preferably repeatedly.

Reference numeral 11 indicates an optical divider means. In the present embodiment said optical divider means consists of two components 11a and 11b. The top component 11a is configured such that the aperture 15 positioned in the bottom component 11b is exposed, i.e. radiation can enter. This is indicated by the reference numeral 12a at the left in the Figure. For fastening the bottom component 11b, the top component 11a must comprise a certain number of ridges. Reference numeral 12b illustrates such a ridge. In a preferred embodiment in particular three such ridges are provided. One of these ridges 12b can be recognized in the cross-sectional view in FIG. 1. The thickness of the optical divider means is designated with d. One can recognize that the aperture 15 extends at a specified angle relative to said thickness.

Beneath the optical divider means 11 the second housing section 8 is arranged. Reference numeral 22 designates an aperture in the bottom housing section. During measuring the measuring surface is positioned beneath said aperture. The width of the aperture 22 is between 10 mm and 50 mm, preferred between 20 mm and 40 mm and particularly preferred in the range of 30 mm.

The detector means 20 is arranged perpendicular to the measuring surface. However, it is also conceivable to arrange the detector means at different positions—or at different angles—relative the measuring surface. The detector means comprises a lens system 23. The focal length of said lens is between 5 mm and 40 mm, preferred between 10 mm and 30 mm and particularly preferred between 15 mm and 20 mm.

Behind said lens 23 there is a filter 24 and one or a plurality of photo diodes 21. Reference numeral 25 designates a diaphragm.

The width of the aperture 15 is approx. 10° and the aperture is positioned at an angle α of approx. 10° to the measuring surface.

In addition, another radiation means 32 and another detector means 38 are provided. By means of these two devices, gloss can be measured at the measuring surface where the angle of incidence of the light emitting from the radiation means 32 is substantially equal to the angle of reflection. The radiation means 32 comprises one or more radiation means 31 and a lens or a lens system 34. The radiation detector means also comprises a lens system 35.

During measuring, light is radiated in the radiation means 1 in the direction of the optical divider means 14. As specified above, the surface of the optical divider means facing the radiation means 1 exhibits light-reflecting and/or diffusing properties. This surface may in particular but not exclusively be a metal reflector or mirrored glass.

As indicated by the dash and dot line, the optical divider means or its surface diffuses and/or reflects the light upwardly in the direction of the dash and dot line. In this way, light from at least one, preferably all of the radiation means 1 is preferably repeatedly reflected within the top housing section before a portion of the light passes through the aperture 15 to enter the bottom housing portion 8. In this way, diffused light is generated which will then be directed to impinge on the measuring surface at an angle determined or predetermined by the aperture 15. The radiation detector means 20 captures a portion of the light diffused and/or reflected off the measuring surface.

Additionally the device may comprise a coating-thickness measurement means for the measuring surface to be examined. Said coating-thickness measurement means may operate both in physical contact with the measuring surface to be examined or without contact. A conceivable position for a coating-thickness measurement means having physical contact is indicated with the reference numeral 50.

In another preferred embodiment motion devices such as—in particular but not exclusively—wheels may be provided which allow displacement of the measuring device relative to the measuring surface. Said motion devices may be equipped with travel measurement means. In this way the measurement results can be captured for example dependent on distances traveled.

Figure 2:
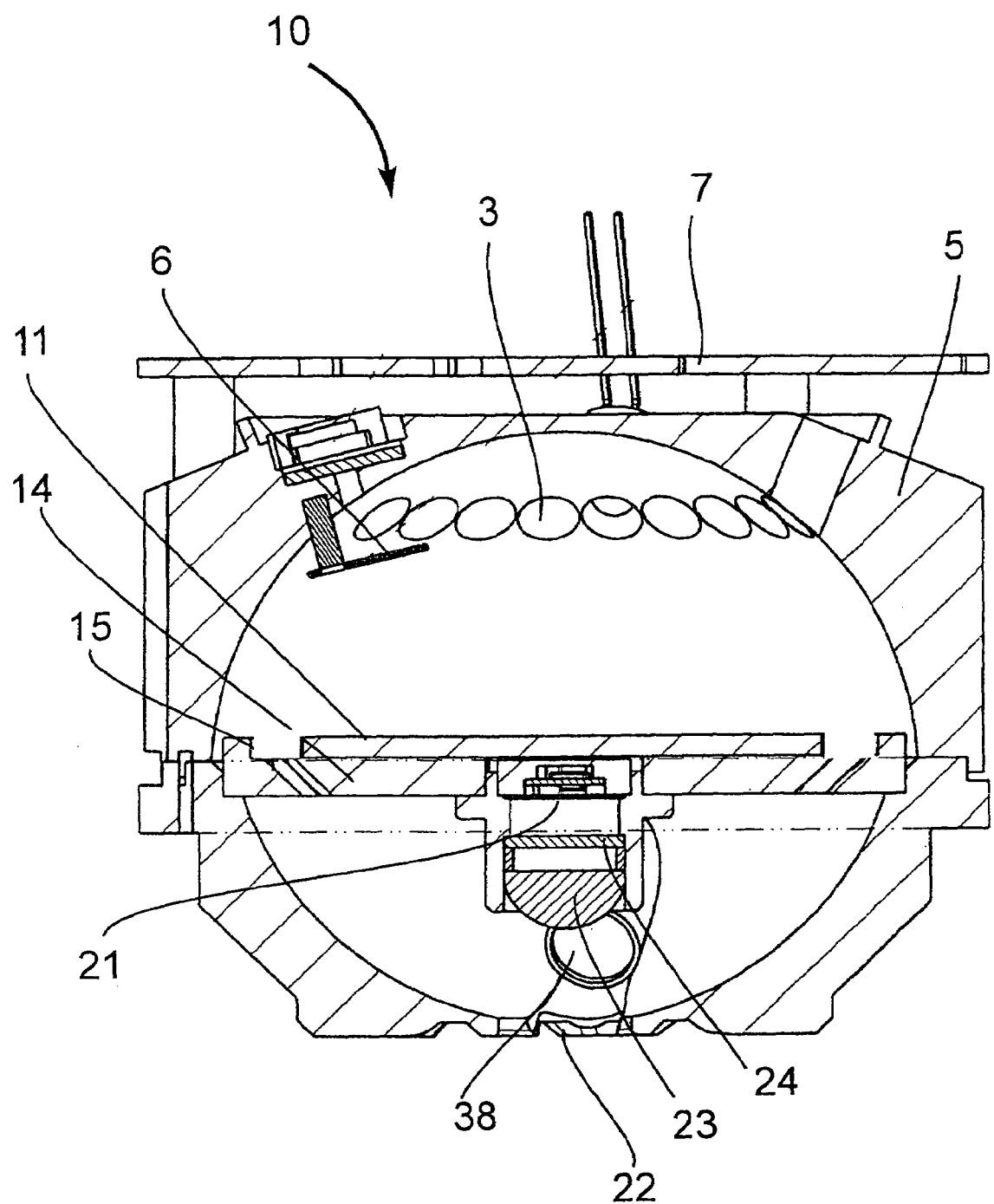
FIG. 2 depicts the device of the invention for determining the properties of surfaces in another embodiment.

FIG. 2 shows another perspective view of the device of the invention, more precisely, from a perspective rotated by 90° compared to FIG. 1. A plurality of apertures 3 is shown intended to receive the radiation means 1. The reference measurement means 6 is illustrated additionally. The reference numeral 38 designates the additional radiation detector means which in this embodiment serves to capture gloss measurements. This embodiment provides a total of 16 light-emitting diodes.

Preferably said light-emitting diodes cover at least the entire span of the spectral range visible to the human eye. To achieve the aim of a substantially constant radiation intensity over the entire range, a plurality of diodes will be arranged in individual spectral ranges.

The invention claimed is:

1. A device for determining the properties of surfaces having:
   at least one first radiation means having at least one radiation source which emits radiation;
   at least one radiation detector means which captures at least a portion of the radiation emitting from the at least one radiation means and then diffused and/or reflected off a measurement surface and emits at least one measurement signal which is characteristic of the reflected and/or diffused radiation;
   an optical divider means having a specified thickness which is positioned in the optical path between the radiation means the radiation detector means;
   wherein said optical divider means comprises at least one aperture at least in sections at a specified angle different from 0 degrees to the thickness of said optical divider means.

2. The Device in particular according to claim 1, wherein a top view of the aperture of the optical divider means it to be substantially a circular slot.

3. The Device according to claim 1, wherein said aperture comprises at least one wall which is substantially defined by the circumferential surface of a cone.

4. The Device according to claim 1, wherein said aperture at its interior surfaces exhibits substantially absorbing properties relative the radiation emitting from the radiation means.

5. The Device according to claim 1, wherein said predetermined angle at which the aperture extends to the thickness of the optical divider means is between 0 degrees and 90 degrees, preferred between 15 and 75 degrees, particularly preferred between 30 degrees and 60 degrees and in particular in the range of 45 degrees.

6. The Device according to claim 1, wherein said optical divider means exhibits at least partially reflecting and/or diffusing properties at one surface facing the at least one radiation means relative the radiation emitting from the radiation means.

7. The Device according to claim 1, wherein said optical divider means configured integrally.

8. The Device according to claim 1, wherein said optical divider means consists at least of two components.

9. The Device according to claim 1, wherein a plurality of first radiation means is provided which are arranged at predetermined positions relative the measuring surface.

10. The Device according to claim 1, wherein said first radiation means are arranged in a first housing section.

11. The Device according to claim 10, wherein said first housing section is substantially hemispherical in shape.

12. The Device according to claim 11, wherein said plurality of radiation means are arranged substantially at an azimuth circle of the substantially hemispherical first housing section.

13. The Device according claim 10, wherein a reference measurement means is arranged in the first housing section.

14. The Device according to claim 13, wherein said reference measurement means comprises a radiation blocking means.

15. The Device according to claim 10, wherein said first housing section exhibits at least at one portion of its surface facing the measunng surface radiation-reflecting and/or radiation-diffusing properties.

16. The Device according to claim 1, wherein said at least one first radiation means comprises a radiation diffusor means.

17. The Device according to claim 16, wherein said at least one radiation diffusor means is selected from a group of radiation diffusor means including radiation diffusor disks, frosted glass disks, diffusor films and the like.

18. The Device according to claim 1, wherein said at least one first radiation means at least one radiation source selected from a group of radiation sources comprising thermal radiation sources, in particular but not exclusively light bulbs, halogen light bulbs, coherent and non-coherent semiconductor radiation sources, gas discharge radiation sources, lasers and the like.

19. The Device according to claim 1, wherein at least two radiation sources exhibit different spectral radiation characteristics.

20. The Device according to claim 19, wherein said at least one radiation source is variable in at least one radiation parameter selected from a group including radiation intensity, radiation wavelength, direction of radiation polarization, temporal radiation intensity modulation and the like.

21. The Device according to claim 1, wherein said at least the first radiation means is arranged in a second housing section.

22. The Device according to claim 21, wherein said second housing section exhibits radiation-absorbing properties at least at a portion of the surfaces facing the radiation detector means.

23. The Device according to claim 21, wherein said substantially no external radiation enters the second housing section unless it has been diffused and/or reflected off the measuring surface.

24. A method for determining the properties of surfaces including the steps:
   emitting a first radiation from at least one first radiation means according to claim 1,
   reflection and/or diffusion of the first radiation off at least one surface;
   directing the radiation through an aperture according to claims 1;
   directing the radiation toward a measuring surface; and
   capturing at least a portion of the radiation diffused and/or reflected off the measurement surface by means of a radiation detector means according to claim 1.

25. The method according to claim 24, wherein said radiation emitting from the first radiation means is repeatedly reflected and/or diffused off the inner surface of a first housing section according to claim 1.

26. Application of the device of claim 1 for determining the properties of surfaces of motor vehicle components.

* * * * *